United States Patent [19]
DiMatteo et al.

[11] Patent Number: 5,810,859
[45] Date of Patent: Sep. 22, 1998

[54] APPARATUS FOR APPLYING TORQUE TO AN ULTRASONIC TRANSMISSION COMPONENT

[75] Inventors: Stephen DiMatteo, Seekonk; Brian Estabrook, Foxboro, both of Mass.

[73] Assignee: Ethicon Endo-Surgery, Inc., Cincinnati, Ohio

[21] Appl. No.: 808,637

[22] Filed: Feb. 28, 1997

[51] Int. Cl.$^6$ .................................................. A61B 17/00
[52] U.S. Cl. ............................................ 606/169; 604/22
[58] Field of Search ........................... 606/167, 169–171, 606/180; 604/22

[56] References Cited

U.S. PATENT DOCUMENTS

| Re. 30,536 | 3/1981 | Perdreaux, Jr. . |
| 2,845,072 | 7/1958 | Shafer . |
| 2,874,470 | 2/1959 | Richards . |

(List continued on next page.)

FOREIGN PATENT DOCUMENTS

| 1098003 | 9/1977 | Canada . |
| 0 495 634 A2 | 1/1992 | European Pat. Off. . |
| 0 624 346 A2 | 5/1994 | European Pat. Off. . |
| 0 624 346 A3 | 5/1994 | European Pat. Off. . |
| 2032-501 | 7/1970 | Germany . |
| 76-18881 | 6/1976 | Germany . |
| 77-05-069 | 2/1977 | Germany . |
| 29 22 239 | 5/1979 | Germany . |
| 37 07 921 A1 | 3/1987 | Germany . |
| 19534618 A1 | 3/1997 | Germany . |
| 56-108085 | of 1981 | Japan . |
| 56-38931 | of 1981 | Japan . |
| 61-265136 | of 1986 | Japan . |
| 61-128954 | 6/1986 | Japan . |
| 63-61609 | 3/1988 | Japan . |
| 63-61609 | 4/1988 | Japan . |
| 63-61609 | 11/1988 | Japan . |
| 2-99049 | of 1990 | Japan . |
| 8-275951 | 4/1995 | Japan . |
| 8-275948 | 10/1996 | Japan . |
| 8-275949 | 10/1996 | Japan . |
| 9-98980 | 4/1997 | Japan . |
| 1388002 A1 | 4/1988 | U.S.S.R. . |
| WO 91/13591 | 3/1991 | WIPO . |
| WO 92/02658 | 7/1991 | WIPO . |
| 0 495 634 A3 | 1/1992 | WIPO . |
| WO 92/14514 | 2/1992 | WIPO . |
| WO 93/14708 | 1/1993 | WIPO . |
| Wo 93/16646 | 1/1993 | WIPO . |
| WO 96/29935 | 4/1996 | WIPO . |
| WP 96/34561 | 5/1996 | WIPO . |

OTHER PUBLICATIONS

Cooper LaserSonics, Inc., Ultrasonic Surgucal Aspirator NS–100 Operator Manual, 1984, pp. 12, 13, 13, 17, and 29–33.
UltraCision Incorporated, The Harmonic Scalpel® For Gynecological Surgery, Product Sheet, Sep. 1992.
UltraCision Incorporated, The Harmonic Scalpel® For General Surgery, Product Sheet Jan. 1993.
Snowden–Pencer, Inc., Endoscopic Plastic Surgery, 1993.
UltraCision Incorporated, Harmonic scalpel® Price List, 1995.
UltraCision Incorporated, Harmonic Scalpel® Operating Manual, Mar. 1995.
Ethicon Endo–Surgery, Inc., Ultracision CS/LCS Layout Brochure, 1996.

Primary Examiner—William Lewis
Attorney, Agent, or Firm—Rockey, Milnamow & Katz, Ltd.

[57] ABSTRACT

An ultrasonic surgical instrument in accordance with the present invention includes a transmission component adapted to receive ultrasonic vibration from a transducer assembly and to transmit the ultrasonic vibration from a first end to a second end. The transmission component has an aperture to allow torque to be coupled to the transmission rod.

28 Claims, 6 Drawing Sheets

U.S. PATENT DOCUMENTS

| | | |
|---|---|---|
| 3,053,124 | 9/1962 | Balamuth et al. . |
| 3,075,288 | 1/1963 | Balamuth et al. . |
| 3,076,904 | 2/1963 | Kleesattel et al. . |
| 3,213,537 | 10/1965 | Balamuth et al. . |
| 3,368,280 | 2/1968 | Fridman et al. . |
| 3,375,583 | 4/1968 | Blank et al. . |
| 3,433,226 | 3/1969 | Boyd . |
| 3,488,851 | 1/1970 | Haydu . |
| 3,489,930 | 1/1970 | Shoh . |
| 3,518,766 | 7/1970 | Burt . |
| 3,526,036 | 9/1970 | Goof . |
| 3,526,792 | 9/1970 | Shoh . |
| 3,589,012 | 6/1971 | Richman . |
| 3,589,363 | 6/1971 | Banko et al. . |
| 3,593,425 | 7/1971 | Robinson . |
| 3,636,943 | 1/1972 | Balamuth . |
| 3,636,947 | 1/1972 | Balamuth . |
| 3,645,255 | 2/1972 | Robinson . |
| 3,654,502 | 4/1972 | Carmona et al. . |
| 3,654,540 | 4/1972 | Honig et al. . |
| 3,657,056 | 4/1972 | Winston et al. . |
| 3,703,037 | 11/1972 | Robinson . |
| 3,792,701 | 2/1974 | Kloz et al. . |
| 3,809,977 | 5/1974 | Balamuth et al. . |
| 3,819,961 | 6/1974 | Bourgeois et al. . |
| 3,842,340 | 10/1974 | Brandquist . |
| 3,930,173 | 12/1975 | Banko . |
| 3,956,826 | 5/1976 | Perdreaux, Jr. . |
| 3,967,143 | 6/1976 | Watanabe et al. . |
| 4,156,157 | 5/1979 | Mabille . |
| 4,169,984 | 10/1979 | Parisi . |
| 4,175,242 | 11/1979 | Kleinschmidt . |
| 4,188,952 | 2/1980 | Loschilov et al. . |
| 4,223,676 | 9/1980 | Wuchinich et al. . |
| 4,227,110 | 10/1980 | Douglas et al. . |
| 4,370,131 | 1/1983 | Banko . |
| 4,371,816 | 2/1983 | Wieser . |
| 4,375,961 | 3/1983 | Brooks . |
| 4,406,284 | 9/1983 | Banko . |
| 4,491,132 | 1/1985 | Aikins . |
| 4,492,574 | 1/1985 | Warrin et al. . |
| 4,522,206 | 6/1985 | Whipple et al. . |
| 4,655,216 | 4/1987 | Tischer . |
| 4,723,545 | 2/1988 | Nixon et al. . |
| 4,750,488 | 6/1988 | Wuchinich et al. . |
| 4,808,153 | 2/1989 | Parisi . |
| 4,816,018 | 3/1989 | Parisi . |
| 4,820,152 | 4/1989 | Warrin et al. . |
| 4,825,865 | 5/1989 | Zelman . |
| 4,832,683 | 5/1989 | Idemoto et al. . |
| 4,867,141 | 9/1989 | Nakada et al. . |
| 4,870,953 | 10/1989 | DonMichael et al. . |
| 4,897,079 | 1/1990 | Zaleski et al. . |
| 4,920,954 | 5/1990 | Alliger et al. . |
| 4,922,902 | 5/1990 | Wuchinich et al. . |
| 4,931,047 | 6/1990 | Broadwin et al. . |
| 4,936,281 | 6/1990 | Stasz . |
| 4,974,590 | 12/1990 | Saito . |
| 4,979,952 | 12/1990 | Kubota et al. . |
| 5,011,471 | 4/1991 | Miyazaki et al. . |
| 5,026,387 | 6/1991 | Thomas . |
| 5,047,043 | 9/1991 | Kubota et al. . |
| 5,057,119 | 10/1991 | Clark et al. . |
| 5,059,210 | 10/1991 | Clark et al. . |
| 5,069,664 | 12/1991 | Guess et al. . |
| 5,112,300 | 5/1992 | Ureche . |
| 5,123,903 | 6/1992 | Quaid et al. . |
| 5,151,084 | 9/1992 | Khek . |
| 5,151,085 | 9/1992 | Sakurai et al. . |
| 5,160,317 | 11/1992 | Costin . |
| 5,167,725 | 12/1992 | Clark et al. . |
| 5,180,363 | 1/1993 | Idemoto et al. . |
| 5,190,517 | 3/1993 | Zieve et al. . |
| 5,248,296 | 9/1993 | Alliger . |
| 5,263,957 | 11/1993 | Davison . |
| 5,269,309 | 12/1993 | Fort et al. . |
| 5,322,055 | 6/1994 | Davison et al. . |
| 5,324,299 | 6/1994 | Davison et al. . |
| 5,342,292 | 8/1994 | Nita et al. . |
| 5,344,420 | 9/1994 | Hilal et al. . |
| 5,346,502 | 9/1994 | Estabrook et al. . |
| 5,380,274 | 1/1995 | Nita . |
| 5,382,162 | 1/1995 | Sharp . |
| 5,397,269 | 3/1995 | Beaty et al. . |
| 5,413,107 | 5/1995 | Oakley et al. . |
| 5,417,672 | 5/1995 | Nita et al. . |
| 5,425,704 | 6/1995 | Sakurai et al. . |
| 5,438,554 | 8/1995 | Seyed-Bolorforosh et al. . |
| 5,449,370 | 9/1995 | Vaitekunas . |
| 5,472,447 | 12/1995 | Abrams et al. . |
| 5,507,738 | 4/1996 | Ciervo . |
| 5,507,743 | 4/1996 | Edwards et al. . |
| 5,509,916 | 4/1996 | Taylor . |
| 5,526,815 | 6/1996 | Granz et al. . |
| 5,540,656 | 7/1996 | Pflueger . |
| 5,542,917 | 8/1996 | Nita et al. . |
| 5,546,947 | 8/1996 | Yagami et al. . |
| 5,562,609 | 10/1996 | Brumbach . |
| 5,562,610 | 10/1996 | Brumbach . |
| 5,582,588 | 12/1996 | Sakurai et al. . |
| 5,606,974 | 3/1997 | Castellano et al. . |
| 5,628,743 | 5/1997 | Cimino . |
| 5,634,466 | 6/1997 | Gruner . |
| 5,653,721 | 8/1997 | Knodel et al. . |
| 5,688,235 | 11/1997 | Sakurai et al. . |

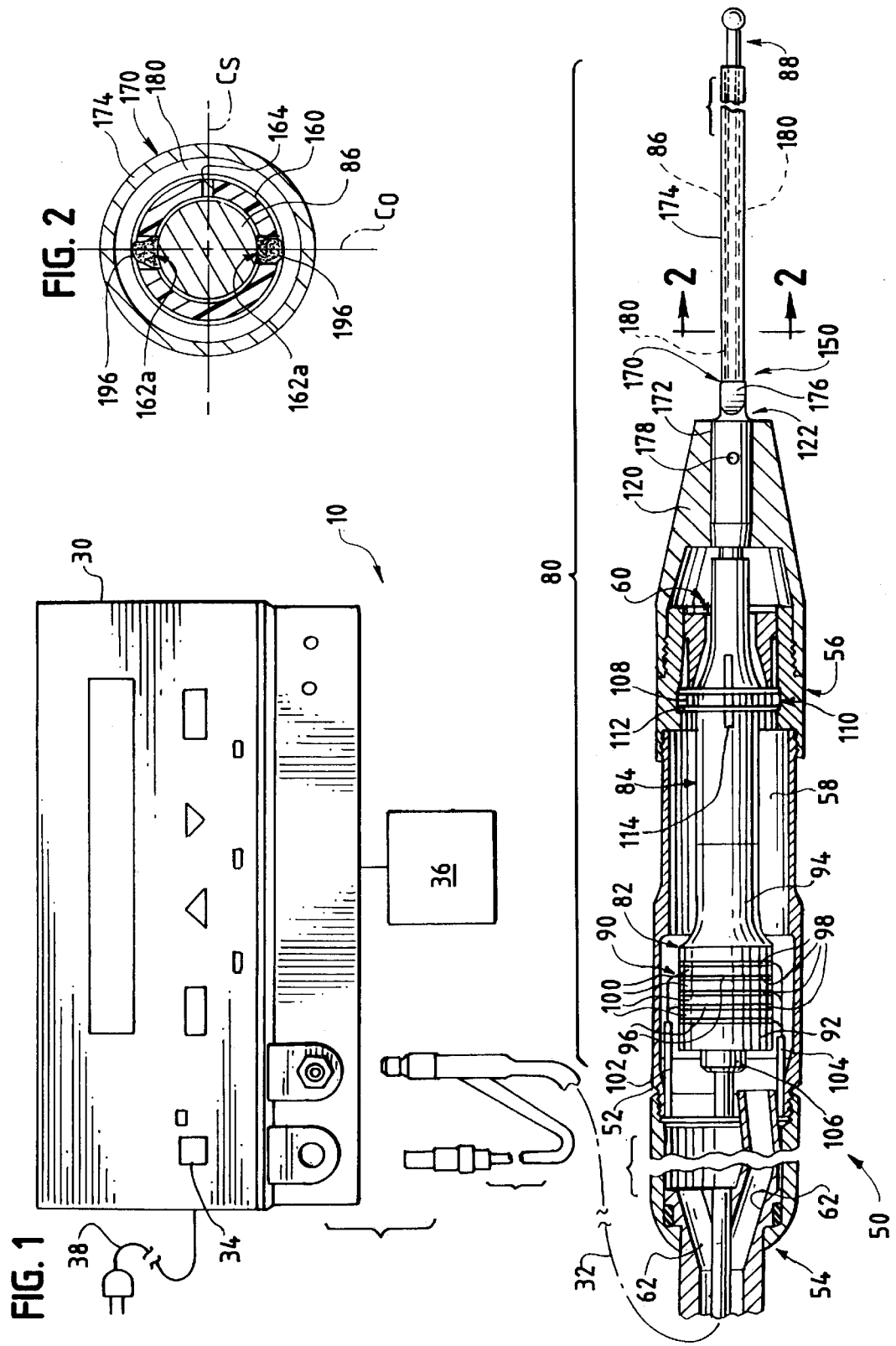

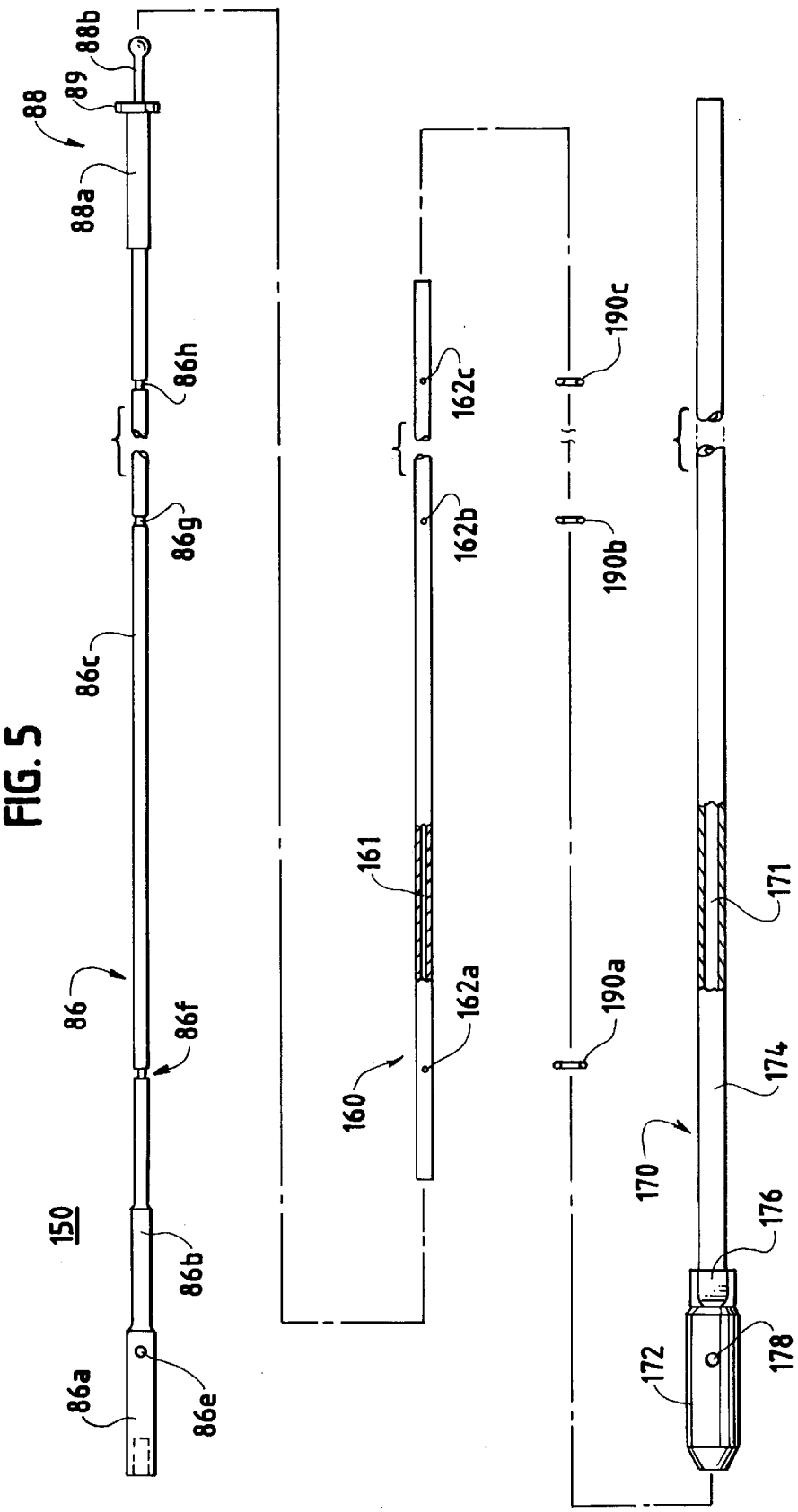

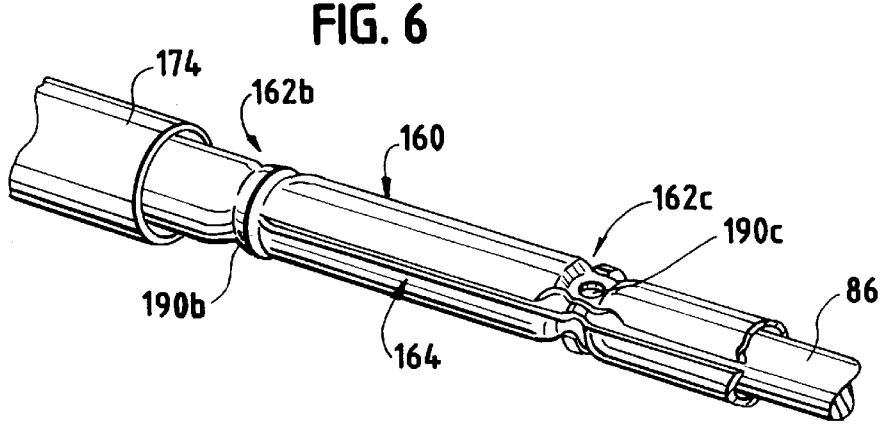
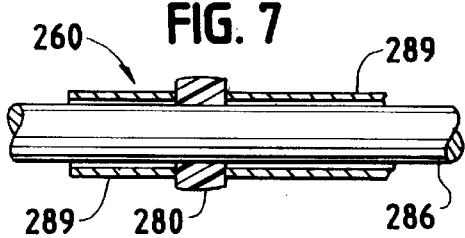
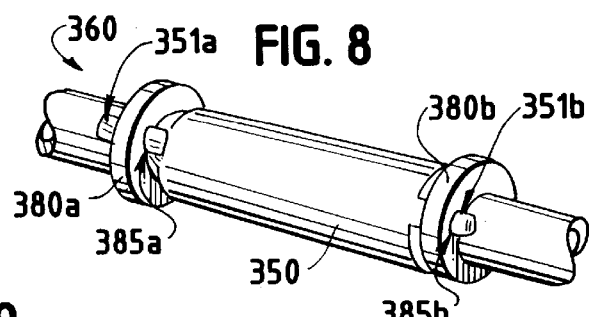
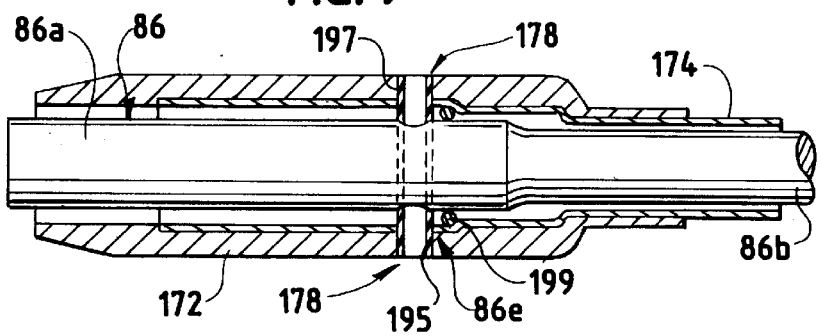
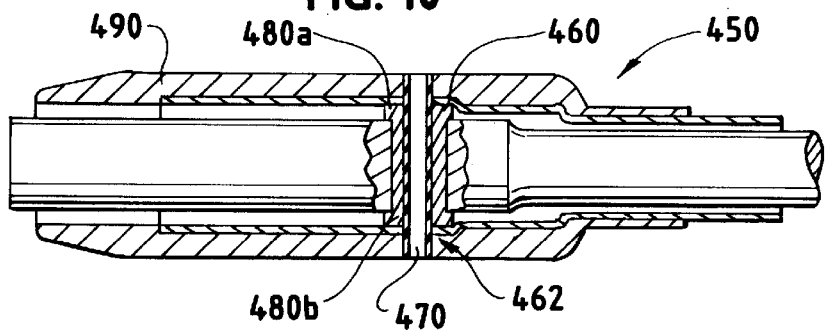

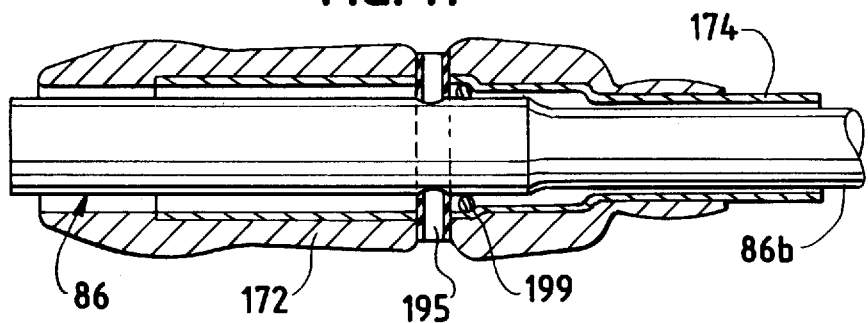
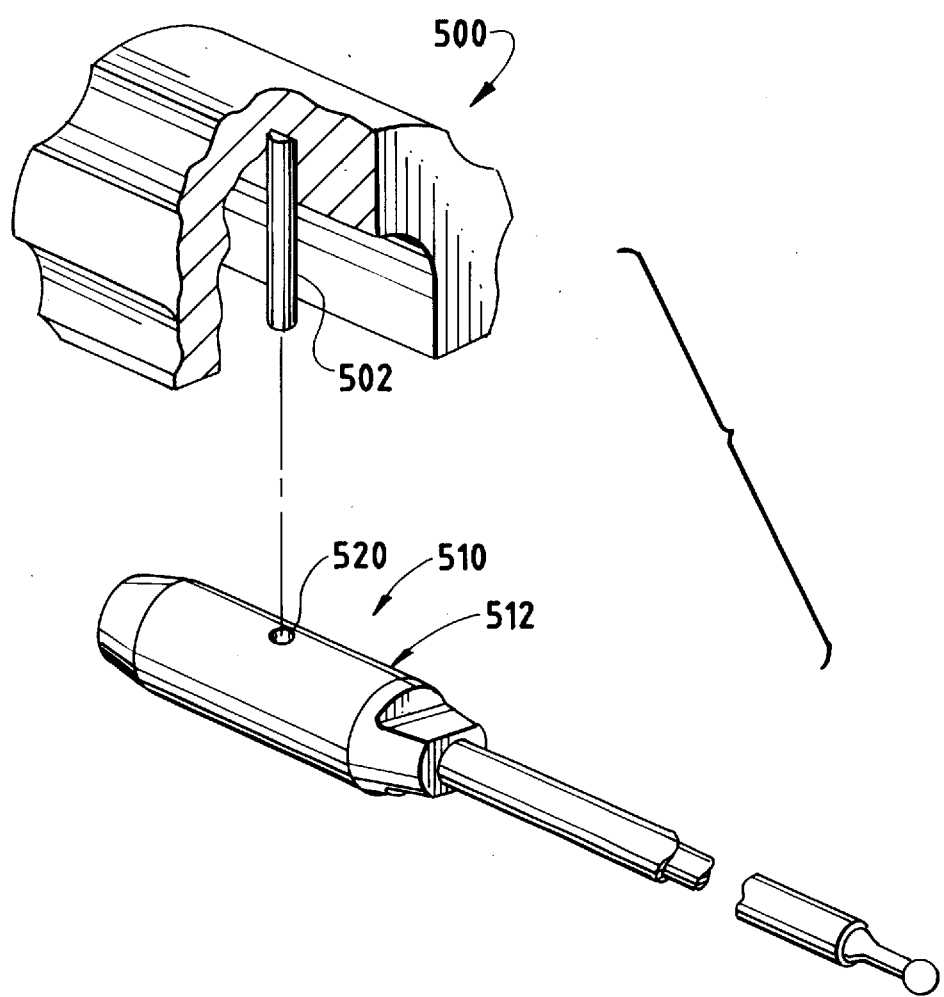

APPARATUS FOR APPLYING TORQUE TO AN ULTRASONIC TRANSMISSION COMPONENT

FIELD OF THE INVENTION

The present invention generally relates to ultrasonic devices. More particularly, the present invention relates to applying torque to an ultrasonic transmission component by a non-vibrating component.

BACKGROUND OF THE INVENTION

Ultrasonic transmission devices are well known for use in a variety of applications, such as surgical operations and procedures. These transmission devices usually include a transducer that converts electrical energy into vibrational motion at ultrasonic frequencies. The vibrational motion is usually transmitted through a mounting device to vibrate a distal end of a working member having a shaft and blade. The shaft typically includes diametrically opposed wrench flats to allow torque to be applied to the working member.

The working member is typically attached to the mounting device by a threaded connection or a screw-type mechanism. Once the working member is threaded onto the mounting device, a wrench may be placed over the working member and applied to the wrench flats of the working member in order to tighten the working member to the mounting device.

Conventional ultrasonic devices typically have wrench flats machined into the working member. For example, U.S. Pat. No. 5,346,502, which is herein incorporated by reference, discloses an ultrasonic instrument that includes a working member having a shaft and a blade. The shaft of the working member includes a pair of flats formed on laterally opposed sides of the shaft to form wrench engaging surfaces. An integral sheath encompasses the shaft, and the sheath has a pair of openings to expose the wrench engaging surfaces externally of the sheath. A wrench may be applied to the engaging surfaces to tighten the shaft to a handpiece. However, the wrench flats are usually costly to manufacture and have to be manufactured to specific tolerances. In addition, material is wasted when the shaft is machined to form the wrench engaging surfaces.

Accordingly, there is a need for improved apparatus for applying torque to a transmission component. It would be beneficial if torque could be applied to transmission component through the use of a non-vibrating component. It would also be desirable to provide a transmission component that is less costly to manufacture.

SUMMARY OF THE INVENTION

In view of the above, the present invention relates to a surgical instrument that enables torque to be applied from a non-vibrating component to an ultrasonic transmission component. The non-vibratory component of the surgical instrument can be coupled to the transmission component so that torque can be applied to the transmission component.

The surgical instrument is relatively simple in design and economical to manufacture. The surgical instrument can be quickly and easily attached to a handpiece assembly and detached from the handpiece assembly. The surgical instrument may be disposed of after a single use and may also prevent reuse of the surgical instrument.

An ultrasonic surgical instrument in accordance with the present invention includes a transmission component adapted to receive ultrasonic vibration from a transducer assembly and to transmit the ultrasonic vibration from a first end to a second end. The transmission component has an aperture to allow torque to be coupled to the transmission rod.

An ultrasonic surgical device in accordance with the present invention includes a transducer assembly adapted to vibrate at an ultrasonic frequency in response to electrical energy. A transmission rod is adapted to receive ultrasonic vibration from the transducer assembly and to transmit the ultrasonic vibrations from a first end to a second end of the transmission rod. The transmission rod has at least one an aperture to allow torque to be coupled to the transmission rod when the first end of the transmission rod is attached to the second end of the mounting device. An end effector is adapted to receive the ultrasonic vibration from the transmission rod and to transmit the ultrasonic vibration from a first end to a second end of the end effector. The second end of the end effector is disposed near an antinode and the first end of the end effector is coupled to the second end of the transmission rod.

It is to be understood that both the foregoing general description and the following detailed description are exemplary and explanatory and are intended to provide further explanation of the invention as claimed.

The invention, together with attendant advantages, will best be understood by reference to the following detailed description of the preferred embodiments of the invention, taken in conjunction with the accompanying drawings.

BRIEF DESCRIPTION OF THE DRAWINGS

FIG. 1 is a cutaway view and in partial cross-section of an embodiment of a surgical system in accordance with the present invention;

FIG. 2 is a cross-sectional view of a surgical instrument of the surgical system of FIG. 1 taken about line 2—2;

FIG. 5 is an exploded view of the surgical instrument of FIG. 4;

FIG. 6 is a partial cutaway perspective view of the surgical instrument of FIG. 3;

FIG. 7 is a partial cross-sectional view of another embodiment of the surgical instrument of FIG. 4 having an outer sheath of surgical instrument removed;

FIG. 8 is a partial perspective view of another embodiment of the surgical instrument of FIG. 3 with the outer sheath removed;

FIG. 9 is a partial cross-sectional view of a hub of the surgical instrument of FIG. 4;

FIG. 10 is a partial cross-sectional view of another embodiment of the hub of the surgical instrument of FIG. 4;

FIG. 11 is a partial cross-sectional view of the hub of FIG. 9 after the hub has been exposed to heat;

FIG. 12 is a perspective view of a wrench configured to tighten an surgical instrument to a handpiece assembly;

DESCRIPTION OF THE PREFERRED EMBODIMENTS

Figure 3:
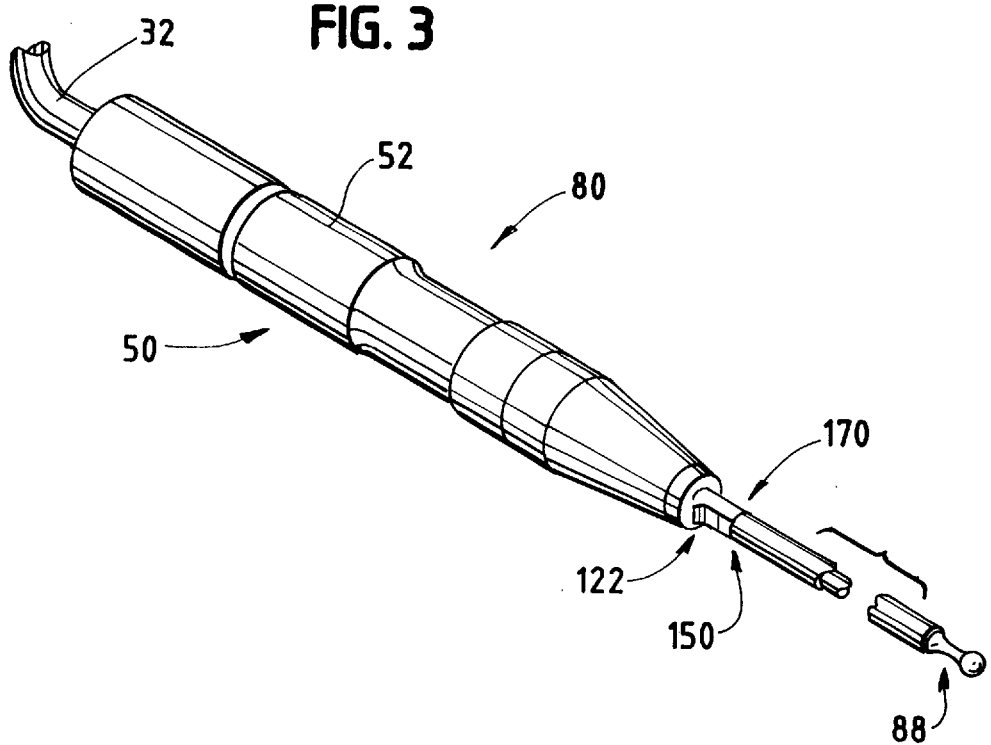
FIG. 3 is a perspective view of a handpiece assembly of the surgical system of FIG. 1.

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Referring now to FIG. 1, a presently preferred embodiment of the surgical system 10 is illustrated. The surgical system 10 generally includes a generator 30, a handpiece assembly 50, an acoustic or transmission assembly 80, an adapter 120, and a surgical instrument or a sheath blade system 150. The generator 30 sends an electrical signal through a cable 32 at a selected amplitude, frequency, and phase determined by a control system of the generator 30. As will be further described, the signal causes one or more piezoelectric elements of the acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude. An end effector 88 at the distal end of the acoustic assembly 80 is placed in contact with tissue of the patient to transfer the ultrasonic energy to the tissue. The cells of the tissue in contact with the end effector 88 of the acoustic assembly 80 will move with the end effector 88 and vibrate.

As the end effector 88 couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the vibrational amplitude of the end effector 88, the amount of pressure applied by the user, and the sharpness of the end effector 88. The end effector 88 of the acoustic assembly 80 in the surgical system 10 tends to focus the vibrational energy of the system 10 onto tissue in contact with the end effector 88, intensifying and localizing thermal and mechanical energy delivery.

As illustrated in FIG. 1, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector 88 at a predetermined vibrational amplitude level. The generator 30 may drive or excite the acoustic assembly 80 at any suitable resonant frequency of the acoustic assembly 80.

When the generator 30 is activated via the triggering mechanism 36, electrical energy is continuously applied by the generator 30 to a transducer assembly 82 of the acoustic assembly 80. A phase locked loop in the control system of the generator 30 monitors feedback from the acoustic assembly 80. The phase lock loop adjusts the frequency of the electrical energy sent by the generator 30 to match a preselected harmonic frequency of the acoustic assembly 80. In addition, a second feedback loop in the control system maintains the electrical current supplied to the acoustic assembly 80 at a preselected constant level in order to achieve substantially constant vibrational amplitude at the end effector 88 of the acoustic assembly 80.

The electrical signal supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector 88 may be controlled by, for example, controlling the amplitude of the electrical signal applied to the transducer assembly 82 of the acoustic assembly 80 by the generator 30.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery. The generator 30 may be any suitable generator, such as Model No. GEN01, available from Ethicon Endo-Surgery, Inc.

Referring to FIGS. 1 and 3, the handpiece assembly 50 of the surgical system 10 includes a multi-piece housing or outer casing 52 adapted to isolate the operator from the vibrations of the acoustic assembly 80. The housing 52 is preferably cylindrically shaped and is adapted to be held by a user in a conventional manner, but may be any suitable shape and size which allows it to be grasped by the user. While a multi-piece housing 52 is illustrated, the housing 52 may comprise a single or unitary component.

The housing 52 of the handpiece assembly 50 is preferably constructed from a durable plastic, such as Ultem®. It is also contemplated that the housing 52 may be made from a variety of materials including other plastics (i.e. liquid crystal polymer (LCP), nylon, or polycarbonate). A suitable handpiece assembly 50 is Model No. HP050, available from Ethicon Endo-Surgery, Inc.

Referring now FIG. 1, the handpiece assembly 50 generally includes a proximal end 54, a distal end 56, and centrally disposed axial opening or cavity 58 extending longitudinally therein. The distal end 56 of the handpiece assembly 50 includes an opening 60 configured to allow the acoustic assembly 80 of the surgical system 10 to extend therethrough, and the proximal end 54 of the handpiece assembly 50 is coupled to the generator 30 by a cable 32. The cable 32 may include ducts or vents 62 to allow air to be introduced into the handpiece assembly 50 to cool the transducer assembly 82 of the acoustic assembly 80.

As shown in FIG. 1, the acoustic assembly 80 generally includes a transducer stack or assembly 82 and a transmission component or working member. The transmission component may include a mounting device 84, a transmission rod or waveguide 86, and an end effector or applicator 88.

The transmission rod 86 and end effector 88 are preferably part of the surgical instrument 150 as further described below.

The components of the acoustic assembly 80 are preferably acoustically tuned such that the length of each component is an integral number of one-half system wavelengths ($n\lambda/2$) where the system wavelength $\lambda$ is the wavelength of a preselected or operating longitudinal vibration frequency f of the acoustic assembly 80. It is also contemplated that the acoustic assembly 80 may incorporate any suitable arrangement of acoustic elements. For example, the acoustic assembly 80 may comprise a transducer assembly and an end effector (i.e., the acoustic assembly 80 may be configured without a mounting device and a transmission rod).

The transducer assembly 82 of the acoustic assembly 80 converts the electrical signal from the generator 30 into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength ($\lambda/4$).

As shown in FIG. 1, the transducer assembly 82 of the acoustic assembly 80, which is known as a "Langevin stack", generally includes a transduction portion 90, a first resonator 92, and a second resonator 94. The transducer assembly 82 is preferably an integral number of one-half system wavelengths ($n\lambda/2$) in length. It is to be understood that the present invention may be alternatively configured to include a transducer assembly comprising a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density and modulus of elasticity of material used in the resonators 92 and 94, and the fundamental frequency of the transducer assembly 82. The second resonator 94 may be tapered inwardly from its proximal end to its distal end to amplify the ultrasonic vibration amplitude.

The transduction portion 90 of the transducer assembly 82 preferably comprises a piezoelectric section of alternating positive electrodes 96 and negative electrodes 98, with piezoelectric elements 100 alternating between the electrodes 96 and 98. The piezoelectric elements 100 may be fabricated from any suitable material, such as, for example, lead zirconate-titanate, lead meta-niobate, lead titanate, or ceramic piezoelectric crystal material. Each of the positive electrodes 96, negative electrodes 98, and piezoelectric elements 100 may have a bore extending through the center. The positive and negative electrodes 96 and 98 are electrically coupled to wires 102 and 104, respectfully. The wires 102 and 104 transmit the electrical signal from the generator 30 to electrodes 96 and 98.

As illustrated in FIG. 1, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94.

The piezoelectric elements 100 are energized in response to the electrical signal supplied from the generator 30 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The mounting device 84 of the acoustic assembly 80 has a proximal end, a distal end, and may have a length substantially equal to an integral number of one-half system wavelengths. The proximal end of the mounting device 84 is preferably axially aligned and coupled to the distal end of the second resonator 94 by an internal threaded connection near an antinode. (For purposes of this disclosure, the term "near" is defined as "exactly at" or "in close proximity to".) It is also contemplated that the mounting device 84 may be attached to the second resonator 94 by any suitable means, and the second resonator 94 and mounting device 84 may be formed as a single or unitary component.

The mounting device 84 is coupled to the housing 52 of the handpiece assembly 50 near a node. The mounting device 84 may include an integral ring 108 disposed around its periphery. The integral ring 108 is preferably disposed in an annular groove 110 formed in the housing 52 of the handpiece assembly 50 to couple the mounting device 84 to the housing 58. A compliant member or material 112, such as a pair of silicone rubber O-rings attached by stand-offs, may be placed between the annular groove 110 of the housing 52 and the integral ring 108 of the mounting device 86 to reduce or prevent ultrasonic vibration from being transmitted from the mounting device 84 to the housing 52.

The mounting device 84 may be secured in a predetermined axial position by a plurality of pins 114, preferably four. The pins 114 are disposed in a longitudinal direction 90 degrees apart from each other around the outer periphery of the mounting device 84. The pins 114 are coupled to the housing 52 of the handpiece assembly 50 and are disposed through notches in the integral ring 108 of the mounting device 84. The pins 114 are preferably fabricated from stainless steel.

The mounting device 84 is preferably configured to amplify the ultrasonic vibration amplitude that is transmitted through the acoustic assembly 80 to the distal end of the end effector 88. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 may be any suitable shape, such as, for example, a stepped horn, a conical horn, an exponential horn, a unitary gain horn, or the like.

The distal end of the mounting device 84 may be coupled to the proximal end of the surgical instrument 150 by an internal threaded connection. It is contemplated that the surgical instrument 150 be attached to the mounting device 84 by any suitable means. The mounting device 84 is preferably coupled to the surgical instrument 150.

Figure 4:
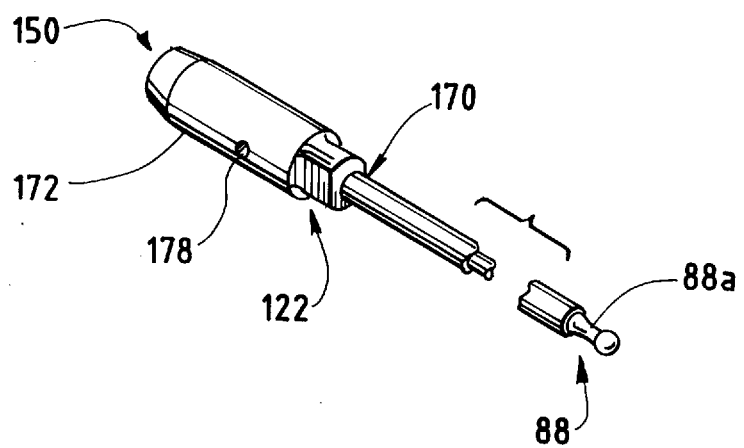
FIG. 4 is a perspective view of the surgical instrument of the surgical system of FIG. 1.

As illustrated in FIGS. 2 and 4, the surgical instrument 150 preferably includes transmission rod 86, end effector 88, an inner sleeve or damping sheath 160, and an outer sheath or sleeve 170. The surgical instrument 150 is preferably attached to and removed from the handpiece assembly 50 as a unit. The surgical instrument 150 is preferably Model No. HDH05, HSH05 or HBC05, available from Ethicon Endo-Surgery, Inc.

The proximal end of the transmission rod 86 of the surgical instrument 150 is preferably detachably coupled to the mounting device 84 of the handpiece assembly 50 near an antinode. The transmission rod 86 may, for example, have a length substantially equal to an integer number of one-half system wavelengths ($n\lambda/2$). The transmission rod 86 is preferably fabricated from a solid core shaft constructed out of material which propagates ultrasonic energy efficiently, such as titanium alloy (i.e., Ti-6Al-4V) or an aluminum alloy. It is contemplated that the transmission rod 86 may be fabricated from any suitable material.

The transmission rod 86 is preferably substantially semi-flexible. It will be recognized that the transmission rod 86 may be substantially rigid or may be a flexible wire. The transmission rod 86 may include one or more opposing flats and may also amplify the mechanical vibrations transmitted through the transmission rod 86 to the end effector 88 as is well known in the art. The transmission rod 86 may further have features to control the gain of the longitudinal vibration along the transmission rod 86 and features to tune the transmission rod to the resonant frequency of the system.

Referring now to FIG. 5, the transmission rod 86 generally has a first section 86*a*, a second section 86*b*, and a third section 86*c*. The first section 86*a* of the transmission rod 86 extends distally from the proximal end of the transmission rod 86. The first section 86*a* has a substantially continuous cross-section dimension. The first section 86*a* preferably has at least one radial hole or aperture 86*e* extending therethrough. The aperture 86*e* extends substantially perpendicular to the axis of the transmission rod 86. The hole 86*e* is preferably positioned at a node but may be positioned at any other suitable point along the acoustic assembly 80. It will be recognized that the aperture 86*e* may have any suitable depth and may be any suitable shape.

The second section 86*b* of the transmission rod 86 extends distally from the first section 86*a*. The second section 86*b* has a substantially continuous cross-section dimension. The diameter of the second section 86*b* is smaller than the diameter of the first section 86*a* and larger than the diameter of the third section 86*c*. As ultrasonic energy passes from the first section 86*a* of the transmission rod into the second section 86*b*, the narrowing of the second section 86*b* will result in an increased amplitude of the ultrasonic energy passing therethrough.

The third section 86*c* extends distally from the distal end of the second section 86*b*. The third section 86*c* has a substantially continuous cross-section dimension. The third section 86*c* may also include small diameter changes along its length. As ultrasonic energy passes from the second section 86*b* of the transmission rod 86 into the third section 86*c*, the narrowing of the third section 86*c* will result in an increased amplitude of the ultrasonic energy passing therethrough.

The third section 86*c* preferably has a plurality of grooves or notches formed in its outer circumference. Preferably, three grooves 86*f,* 86*g,* and 86*h* are formed in the third section 86*c* of the transmission rod 86. The grooves 86*f,* 86*g,* and 86*h* may be located at nodes of the transmission rod 86 or any other suitable point along the transmission rod 86 to act as alignment indicators for the installation of the damping sheath 160 and compliant members 190*a,* 190*b,* and 190*c* during manufacturing. It is contemplated that any suitable number of grooves may be formed in the transmission rod 86.

It will be recognized that the transmission rod 86 may have any suitable cross-sectional dimension. For example, the transmission rod 86 may have a substantially uniform cross-section or the transmission rod 86 may be tapered at various sections or may be tapered along its entire length.

The distal end of the transmission rod 86 may be coupled to the proximal end of the end effector 88 by an internal threaded connection, preferably near an antinode. It is contemplated that the end effector 88 may be attached to the transmission rod 86 by any suitable means, such as a welded joint or the like. Although the end effector 88 may be detachable from the transmission rod 86, the end effector 88 and transmission rod 86 are preferably formed as a single unit.

The end effector 88 preferably has a length substantially equal to an integral multiple of one-half system wavelengths ($n\lambda/2$). The distal end of the end effector 88 is disposed near an antinode in order to produce the maximum longitudinal deflection of the distal end. When the transducer assembly 82 is energized, the distal end of the end effector 88 is configured to move longitudinally in the range of, for example, approximately 10 to 500 microns peak-to-peak, and preferably in the range of about 30 to 100 microns at a predetermined vibrational frequency, and most preferably at about 90 microns.

The end effector 88 of the acoustic assembly 80 generally has a first section 88*a* and a second section 88*b*. The first section 88*a* of the end effector 88 extends distally from the distal end of the third section 86*c* of the transmission rod 86. The first section 88*a* has a substantially continuous cross-section dimension. The diameter of the first section 88*a* of the end effector 88 is larger than the diameter of the second section 88*b*. The first section 88*a* may also have a sealing ring 89 disposed near its distal end, preferably near a node. As the ultrasonic energy passes from the first section 88*a* into the second section 88*b*, the magnitude of the ultrasonic vibration transmitted increases. It will be recognized that the end effector 88 may have any suitable cross-section dimension.

The end effector 88 is preferably made from a solid core shaft constructed of material such as, for example, a titanium alloy (i.e., Ti-6Al-4V) or an aluminum alloy which propagates ultrasonic energy. It is contemplated that the end effector 88 may be fabricated from other suitable materials. The distal end of the end effector 88 may have a surface treatment to improve the delivery of energy and desired tissue effect. For example, the end effector 88 may be micro-finished, coated, plated, etched, grit-blasted, roughened or scored to enhance coagulation in tissue or to reduce adherence of tissue and blood to the end effector. Additionally, the distal end of the effector 88 may be sharpened or shaped to enhance its energy transmission characteristics. For example, the end effector 88 may be blade shaped, hook shaped, ball shaped, or any other suitable shape.

Referring now to FIGS. 5 and 6, the damping sheath 160 of the surgical instrument 150 loosely surrounds at least a portion of the transmission rod 86. The damping sheath 160 may be positioned around the transmission rod 86 to dampen or limit transverse side-to-side vibration of the transmission rod 86 during operation. The damping sheath 160 preferably surrounds part of the third section 86c of the transmission rod 86 and is coupled or attached to the transmission rod 86 near one or more nodes. The damping sheath 160 is only attached to the transmission rod at the nodal points thereby preventing the sheath from otherwise adhering to the outer surface of the transmission rod 86.

In a present embodiment, the damping sheath extends along substantially the entire length of the transmission rod. The damping sheath 160 may extend less than half the entire length of the transmission rod 86 and may be positioned around any suitable portion of the transmission rod 86. The sheath 160 preferably extends over at least one antinode of transverse vibration, and more preferably, a plurality of antinodes of transverse vibration. The damping sheath 160 preferably has a substantially circular cross-section. It will be recognized that the damping sheath 160 may have any suitable shape to fit over the transmission rod and be any suitable length.

The damping sheath 160 is preferably in light contact with the transmission rod 86 to absorb unwanted ultrasonic energy from the transmission rod 86. The damping sheath 160 reduces the amplitude of non-axial vibrations of the transmission rod 86, such as, unwanted transverse vibrations associated with the longitudinal frequency of 55,500 Hz as well as other higher and lower frequencies.

The damping sheath 160 is constructed of a polymeric material, preferably with a low coefficient of friction to minimize dissipation of energy from the axial motion or longitudinal vibration of the transmission rod 86. The polymeric material is preferably floura-ethylene propene (FEP) which resists degradation when sterilized using gamma radiation. It will be recognized that the damping sheath be fabricated from any suitable material, such as, for example, polytetra-floura ethylene (PTFE).

The damping sheath 160 is more effective than using silicone rubber rings located only at nodes of longitudinal vibration because the damping sheath 160 can dampen transverse motion occurring near multiple antinodes of the unwanted vibration which are located randomly along the length of the transmission rod 86 relative to the nodes and antinodes of the desired longitudinal vibration. The damping sheath 160 can also effectively absorb the unwanted ultrasonic energy without using a damping fluid, which is more efficient and is advantageous in situations where the use of fluid may be inconvenient or impractical.

Referring now to FIGS. 2, 5 and 6, the damping sheath 160 has an opening 161 extending therethrough, one or more pairs of diametrically opposed openings 162a, 162b, and 162c, and a longitudinal slit or slot 164. The openings 162a, 162b, and 162c are positioned over or near the grooves 86f, 86g, and 86h of the transmission rod 86, respectively. The openings 162a, 162b, and 162c of the damping sheath 160 are preferably cylindrically shaped and have a diameter of about 0.078 inches. It is contemplated that the damping sheath 160 may have any suitable number of openings, and the openings may be any suitable shape and size without departing from the spirit and scope of the present invention.

The length of the damping sheath 160 is preferably between about 9.73–9.93 inches when the transmission rod has a length of about 12 inches. The distance from the proximal end of the damping sheath 160 to the opening 162a of the damping sheath is about 0.675 inches, and the distance from the proximal end of the damping sheath 160 to the opening 162b is about 4.125 inches. The distance from the proximal end of the damping sheath 160 to the opening 162c is about 9.325 inches. It is contemplated that the damping sheath 160 may have any suitable length and the openings can be at any suitable position along the damping sheath 160.

The thickness of the damping sheath 160 is preferably between about 0.007 and 0.009, and the opening 161 (see FIG. 5) of the damping sheath 160 has a diameter between about 0.112–0.116. It is contemplated that the thickness of the damping sheath and the diameter of the opening 161 may be any suitable size without departing from the spirit and scope of the present invention.

The slit 164 of the damping sheath 160 allows the damping sheath 160 to be assembled over the transmission rod 86 from either end. Without the slit 164, the sheath may not fit over the larger cross-sectional diameters of the transmission rod 86 and the damping sheath 160 may not be able to loosely contact the transmission rod 86. It will be recognized that the damping sheath 160 may have any suitable configuration to allow the damping sheath 160 to fit over the transmission rod 86. For example, the damping sheath 160 may be formed as a coil or spiral or may have patterns of longitudinal and/or circumferential slits or slots. It is also contemplated that the damping sheath may be fabricated without a slit and the transmission rod may be fabricated from two or more parts to fit within the damping sheath.

The slit 164 of the damping sheath 160 preferably runs parallel to the axis of the damping sheath 160 and extends from the proximal end of the damping sheath 160 to its distal end. The width of the slit 164 preferably is about 0 to 0.010 inches. A center line $C_S$ extending through the slit 164 is preferably about 75 to 105 degrees from a center line $C_O$ extending through the center of the openings 162a of the damping sheath 160 as illustrated in FIG. 2. It will be recognized that the width of the slit 164 may be any suitable size.

Referring now to FIGS. 5 and 6, the damping sheath 160 is coupled to or maintained on the transmission rod 86 by compliant members such as, for example, fenders or O-rings. The compliant members 190a, 190b, and 190c may be fabricated from polymeric material, such as, for example, silicone rubber. It will be recognized that the compliant members may be constructed from any suitable material.

The compliant members 190a, 190b, and 190c are disposed around the periphery of the damping sheath 160 and are circumferentially spaced from one another. The compliant members 190a, 190b, and 190c extend across the openings 162a, 162b, and 162c of the damping sheath 160, respectively, to allow the compliant members 190a, 190b, and 190c to be attached to the transmission rod 86. The compliant members 190a, 190b, and 190c are preferably disposed around the transmission rod 86 near nodes in order to minimize damping of the desired longitudinal vibration energy.

The compliant members 190a, 190b, and 190c are preferably secured to the transmission rod 86 by an adhesive 196, such as, for example, cyanoacrylate. The compliant members 190a, 190b, and 190c are joined to the transmission rod 86 at the points where the openings 162a, 162b, and 162c of the damping sheath 160 allow the transmission rod 86 to be exposed. It is contemplated that the compliant members 190a, 190b, and 190c may be secured to the transmission rod 86 by any suitable means.

The contact between the compliant members 190a, 190b, and 190c and the damping sheath 160 improves the damping effectiveness by preventing large amplitude vibrations or rattling of the damping sheath 160 itself. The compliant members also prevent loss of vibrational energy from the transmission rod 86 which might occur under side loading or bending conditions which would otherwise cause indirect contact between the transmission rod 86 and the outer sheath 170 through the damping sheath.

Referring now to FIG. 7, another embodiment of a damping sheath 260 to dampen unwanted vibration along a transmission rod 286 is illustrated. The damping sheath 260 preferably includes one or more compliant members 280 (one being shown) and one or more sleeves 289a and 289b (two being shown). The compliant members 280 are preferably simultaneously created and attached to the transmission rod 286 using an insert molding process as known in the art. Each sleeve of the damping sheath 260 is captured longitudinally between the compliant members 280 so that the damping sheath 260 is maintained loosely in place around the transmission rod 286. The compliant members 280 are preferably positioned at nodes of longitudinal vibration of the transmission rod 286 and are constructed of polymeric material, preferably silicone rubber. It is contemplated that the compliant members may be constructed of any suitable material and may be positioned at any suitable point along the transmission rod.

Referring now to FIG. 8, another embodiment of a damping sheath 360 to dampen unwanted vibration along a transmission rod is illustrated. The damping sheath 360 preferably includes at least one sleeve or sheath 350 anchored by one or more compliant members 380a and 380b (two being shown). The compliant members 380a and 380b are substantially similar in construction and function as the compliant members described above except that the compliant members 380a and 380b are created by insert molding over the transmission rod with the sleeve 350 already in place. The sleeve 350 preferably has a pair of flanges or projections 351a and 351b extending longitudinally from each end that are captured in longitudinal slots 385a and 385b, respectfully, of the compliant members 380a and 380b.

Referring now to FIGS. 4 and 5, the outer sheath 170 of the surgical instrument 150 surrounds the transmission rod 86 and the damping sheath 160. As shown in FIG. 5, the outer sheath 170 preferably has an opening 171 extending longitudinally therethrough. The inside diameter of the opening 171 is spaced at a predetermined distance from the transmission rod 86 and damping sheath 160. The compliant members 190a, 190b, and 190c are positioned between the outer sheath 170 and the damping sheath 160 to reduce the transmission of vibration to the outer sheath.

The outer sheath 170 generally includes a hub 172 and an elongated tubular member 174. The tubular member 174 may be fabricated from stainless steel. It will be recognized that the tubular member may be constructed from any suitable material and may be any suitable shape.

The hub 172 of the outer sheath 170 is preferably constructed of a material which is designed to soften, melt, or otherwise deform or distort, when exposed to a heated environment, such as, for example, in a steam sterilizer or autoclave. The hub 172 may be fabricated from polycarbonate, preferably an Eastman Estalloy (DA003) copolyester/polycarbonate alloy available from Eastman. It is contemplated that the hub may be fabricated from any other suitable material. It will be recognized that the hub or deformable material may be positioned at any point along the transmission rod to prevent an adapter 120 from sliding over the surgical instrument 150 as further described below. It is also contemplated that the adapter 120 may alternatively be configured to fit within a hub.

The hub 172 preferably has a substantially circular cross-section and fits snugly within the lumen 122 of the adapter 120. The snug fit of hub within the lumen of the adapter 120 provides lateral support to the hub 172 and sheath 174 from the handpiece assembly. This protects the transmission rod 86 from bearing large forces when side loads are placed on the surgical instrument 150. An O-ring 199 is also preferably disposed in the hub at a node to isolate the hub 172 from the transmission rod 86.

As shown in FIGS. 4 and 9, the hub 172 preferably has a pair of holes or openings 178 on opposite sides of the hub 172 to allow the hub 172 to be coupled to the transmission rod 86 so that the transmission rod will rotate when the hub is turned. The holes 178 of the hub 172 are aligned with the hole 86e in the transmission rod 86 to form a passageway as illustrated in FIG. 9. A coupling member 195, such as, for example, a pin, may be positioned within the passageway. The coupling member 195 may be held in the passageway of the transmission rod 86 and hub 172 by any suitable means, such as, for example, an cyanoacrylate adhesive, or the coupling member may be detachable from the transmission rod 86 and hub 172. The coupling member 195 allows rotational torque applied to the hub 172 of the outer sheath 170 to be transmitted to the transmission rod 86 in order to tighten it onto the mounting device of the handpiece assembly 50. The coupling member 195 may also hold the outer sheath 170 in place with respect to the transmission rod 86.

As illustrated in FIG. 4, the hub 172 of the outer sheath 170 includes wrench flats 176 on opposites sides of the hub 172. The wrench flats 176 are preferably formed near the distal end of the hub 172. The wrench flats 176 of the hub 172 allow torque to be applied to the hub 172 to tighten the transmission rod 86 mounting device of the handpiece assembly.

The coupling member 195 may be vibrationally isolated from the transmission rod 86. As shown in FIG. 9, a compliant or isolation member 197 surrounds the coupling member 195. The compliant member 197 may be a thin silicone rubber layer, a sleeve of silicone rubber, or any other suitable compliant material. The compliant member 197 prevents conduction of vibration from the transmission rod 86 to the coupling member 195. As a result, the compliant member 197 prevents audible noise and power loss from the vibration of the coupling member 195. The compliant member 197 is preferably thin enough so that torque can be applied from the outer sheath 170 to rotate the transmission rod 86.

It will also be recognized that the coupling member and a compliant cushion can be permanently attached to the surgical instrument, as described above, and such that the coupling member extends radially beyond the outside diameter of the transmission rod, to allow the coupling member to engage an integral or a separate and removable wrench handle.

Referring now to FIG. 10, another embodiment of a hub of a surgical instrument 450 is illustrated. The surgical instrument 450 is substantially similar to the construction and function of the surgical instrument 150 described above except that a compliant member 460 is formed within an aperture or passageway 462 of the transmission rod. The compliant member 460 is preferably insert molded over the transmission member and extends through the aperture through the transmission rod to reduce the transmission of vibration from the transmission rod to the coupling member 470. The compliant member 460 may be formed with shoulders 480a and 480b between a hub 490 of a sheath and the transmission rod to support against radial movement of the transmission rod versus the hub.

The coupling member may also be attached to a tool, such as, for example, a wrench, so that a user may insert the coupling member into an aperture of the transmission rod of the surgical instrument in order to tighten it to the handpiece assembly. As shown in FIG. 12, a wrench handle 500 may be used to tighten a surgical instrument 510 onto a handpiece assembly. The wrench handle 500 preferably has a coupling member 502, such as a pin, attached thereto. The surgical instrument 510 is substantially similar in construction and function of the surgical instrument 510 except that the hub 512 may not have wrench flats.

The coupling member 502 is inserted through a hole or aperture 520 that extends through an upper portion of the hub 572 and into an aperture of the transmission rod. Torque may then be applied to the transmission rod via the wrench handle 500. After torque is applied, the wrench handle 500 may be removed from the surgical instrument 510 prior to activating the device. Accordingly, the coupling member 502 may not have a compliant member or coating since it is not attached during ultrasonic actuation. It is also contemplated that a torque limiting device may be incorporated into the wrench handle 500. For example, U.S. Pat. Nos. 5,507,119 and 5,059,210, which are herein incorporated by reference, disclose torque wrenches for attaching and detaching a transmission rod to a handpiece assembly.

Referring now to FIGS. 1–4, the procedure to attach and detach the surgical instrument 150 from the handpiece assembly 50 will be described below. When the physician is ready to use the surgical instrument, the physician simply attaches the surgical instrument 150 onto the handpiece assembly. To attach the surgical instrument 150 to a handpiece assembly 50, the distal end of the mounting device 84 is threadedly connected to the proximal end of the transmission rod 86. The surgical instrument 150 is then manually rotated in a conventional screw-threading direction to interlock the threaded connection between the mounting device 80 and the transmission rod 86.

Once the transmission rod 86 is threaded onto the mounting device 84, a tool, such as, for example, a torque wrench, may be placed over the surgical instrument 150 to tighten the transmission rod 86 to the mounting device 84. The tool may be configured to engage the wrench flats 176 of the hub 172 of the outer sheath 170 or the tool may have a coupling member or pin that is inserted into a hole or aperture 86e of the transmission rod in order to tighten the transmission rod 86 onto the mounting device 84. As a result, the rotation of the hub 172 will rotate the transmission rod 86 until the transmission rod 86 is tightened against the mounting device 84 at a desired and predetermined torque.

When the transmission rod 86 of the surgical instrument 150 is attached to the mounting device 84 of the handpiece assembly 50, the junction between the transmission rod 86 and the mounting device 84 produces a relatively high axial compression force that is substantially uniformly distributed symmetrically about the longitudinal axis of the threaded connection of the mounting device and transmission rod 86 to efficiently transfer mechanical or ultrasonic vibrations across the junction. As a result, the ultrasonic vibrational motion may travel along the longitudinal axis of the joined components with minimal losses and minimal conversion of longitudinal energy into transverse vibrations.

Once the transmission rod 86 is tightened onto the mounting device, the adapter 120 of the surgical system 10 is axially slipped over the surgical instrument 150 and attached to the distal end of the handpiece assembly 50. The adapter 120 may be threaded or snapped onto the distal end of the housing 52.

The adapter 120 includes an axial bore or lumen 122 configured to snugly fit over the hub 172 of the surgical instrument 150. The lumen 122 has an inner surface having a selected geometric configuration, such as, for example, substantially cylindrically or elliptically shaped. Preferably, the lumen 122 has substantially the same shape as the hub 172 of the outer sheath 170, but has a slightly larger diameter than the hub 172 to allow the lumen 122 of the adapter 120 to pass over the hub 172. The hub 172 allows precise engagement with the inner diameter of the lumen of the adapter 120 in order to ensure alignment of the transmission rod 86 the handpiece assembly 50.

The adapter 122 may be fabricated from Ultem® or liquid crystal polymer (LCP). The adapter 132 may also be made from a variety of materials including other plastics, such as a polyetherimide, nylon or polycarbonate, or any other suitable material.

To detach the surgical instrument 150 from the mounting device 84 of the handpiece assembly 50, the tool may be slipped over the transmission rod 86 and rotated in the opposite direction, i.e., in a direction to unthread the transmission rod 86 from the mounting device 84. When the tool is rotated, the hub 172 allows torque to be applied to the transmission rod 86 through the coupling member 195, such as, for example, a pin, to allow a relatively high disengaging torque to be applied to rotate the transmission rod 86 in the unthreading direction. As a result, the transmission rod 86 loosens from the mounting device 84. Once the transmission rod 86 is removed from the mounting device 84, the entire surgical instrument 150 may be thrown away.

Since the hub of the surgical instrument 150 is constructed of a material which distorts at temperatures normally used for heat sterilization in hospitals, any attempt to heat sterilize the surgical instrument 150 for reuse results in a deformed hub to prevent the surgical instrument 150 from being used again. As shown in FIG. 11, when the hub 172 is sterilized with steam or otherwise exposed to heat and/or high humidity, the outside diameter of the hub 172 deforms or becomes irregular upon resterilization in, for example, a steam sterilizer or autoclave. As a result, the lumen 122 of the adapter 120 cannot pass or slide over the hub 172 of the surgical instrument 150. Thus, the adapter 122 cannot be attached to the handpiece assembly thereby preventing a user from reusing the surgical instrument 120.

Figure 13:
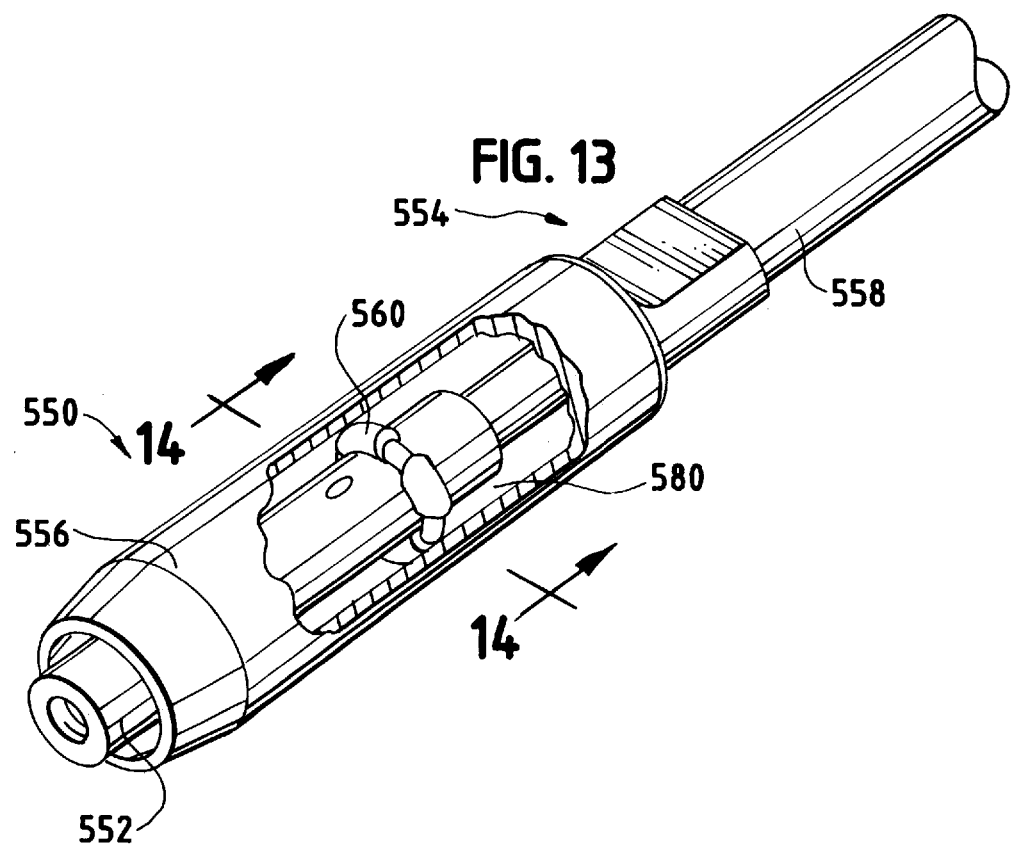
FIG. 13 is a partial perspective view of another embodiment of the surgical instrument of FIG. 3.
Figure 14:
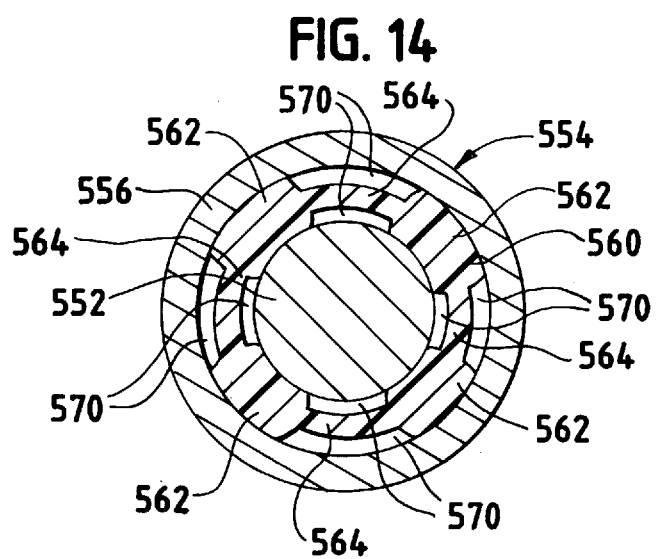
FIG. 14 is a cross-sectional view of the surgical instrument of FIG. 13 taken about line 14.

Referring now to FIGS. 13 and 14, another embodiment of a single use surgical instrument 550 is illustrated. The surgical instrument 550 preferably includes a transmission component 552, a sheath 554, and one or more support members 560 (one being shown), such as, for example, an O-ring. The transmission component 552 may be substantially similar in construction and function as the transmission components as described above. It is contemplated that the transmission component 552 may be any suitable transmission component.

The sheath 554 of the surgical instrument 550 generally includes a hub 556 and an elongated tubular member 558.

The hub 556 and the tubular member 558 may be substantially similar in construction and function as the hub and tubular member as described above. It will be recognized that the hub 556 and tubular member 558 may be constructed from any suitable material and may be any suitable shape.

The support member 560 is disposed around the outer periphery of the transmission component 552. The support member 560 positions the transmission component 552 with the hub 556 and reduces vibration from being transmitted from the transmission component 552 to the hub 556. The support member 560 is preferably positioned at a node of longitudinal vibration of the transmission component 552 and is constructed of polymeric material, preferably silicone rubber. It is contemplated that the support member may be constructed of any suitable material and may be positioned at any suitable point along the transmission rod.

The support member 560 preferably has one or more sections of varying diameter. As illustrated in FIG. 14, the support member 560 has four sections 562 of a first diameter and four sections 564 of a second diameter. The second diameter of the four sections 564 is smaller than the first diameter of the four sections 562. The four sections 564 create spaces or channels 570 between the support member 560 and the hub 556 and the support member 560 and the transmission component 560. The channels 570 allow the surgical instrument to be initially sterilized by the manufacturer with, for example, ethylene oxide (ETO). However, when resterilized, the channels 570 allow sterilizing agents, such as, for example, gases and fluids, to pass by the support member 560 to enter a gap or space 580 between the sheath and transmission component 560. For example, he channels 570 further allow sterilizing fluids to enter the gap 580 between the sheath and transmission component 560 when the surgical instrument is submersed in cleaning fluids. Once the sterilizing agents have entered into the gap 580, the agents become trapped because of the close fit of the components. As a result, significant loading will be added to the ultrasonic transmission component and the ultrasonic transmission rod will not be able to resonate, thereby preventing reuse of the surgical instrument. It is contemplated that the support member 560 may be any suitable shape to allow fluid to flow into the space between the hub and the transmission component. It will be recognized that the transmission component may have grooves or slots on its outer surface and the sheath may have grooves or slots on its inner surface to allow the passage of gases and fluid into the gap.

The surgical instruments of the present invention are preferably configured and constructed to permit passage of ultrasonic energy through the ultrasonic transmission rod with minimal lateral side-to-side movement of the ultrasonic transmission rod while, at the same time, permitting unrestricted longitudinal forward/backward vibrational or movement of the ultrasonic transmission rod.

The surgical instruments allow torque to be applied to the transmission component by a non-vibratory member. The surgical instruments also allow use of the existing torque wrenches without requiring large diameter wrench flats or surfaces. Since no large wrench flat features are needed, the transmission rod can be machined from small diameter stock. Accordingly, the ultrasonic transmission rod can be made smaller reducing the size of the entire ultrasonic package.

The surgical instruments allow medical personnel to quickly and easily attach the surgical instruments to the handpiece. The surgical instrument is desirably and beneficially applied to and removed from a handpiece as a unit. The surgical instruments can be disposed of after a single use.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. An ultrasonic surgical device comprising:
    a transducer assembly adapted to vibrate at an ultrasonic frequency in response to electrical energy;
    a mounting device having a first end and a second end, the mounting device adapted to receive ultrasonic vibration from the transducer assembly and to transmit the ultrasonic vibration from the first end to the second end of the mounting device, the first end of the mounting device coupled to the transducer assembly;
    a transmission rod having a first end and a second end, the transmission rod adapted to receive ultrasonic vibration from the mounting device and to transmit the ultrasonic vibrations from the first end to the second end of the transmission rod, the transmission rod having an aperture to allow torque to be applied to the transmission rod when attaching the first end of the transmission rod to the second end of the mounting device; and
    an end effector having a first end and a second end, the end effector adapted to receive the ultrasonic vibration from the transmission rod and to transmit the ultrasonic vibration from the first end to the second end of the end effector, the second end of the end effector disposed near an antinode and the first end of the end effector coupled to the second end of the transmission rod.

2. The device of claim 1 further comprising a coupling member disposed in the aperture of the transmission rod while the transmission rod is vibrating.

3. The device of claim 1 further including a wrench having a coupling member, the coupling member configured to be inserted into the aperture of the transmission rod.

4. The device of claim 1 further comprising a non-vibrating member surrounding a portion of the transmission rod, the non-vibrating member including at least one opening coaxially aligned with the aperture of the transmission rod; and
    a coupling member positionable in the at least one opening of the non-vibrating member and the aperture of the transmission rod so that the non-vibrating member can rotate the transmission rod.

5. An ultrasonic surgical device comprising:
    a transducer assembly adapted to vibrate at an ultrasonic frequency in response to electrical energy;
    a transmission rod having a first end and a second end, the transmission rod adapted to receive ultrasonic vibration from the transducer assembly and to transmit the ultrasonic vibrations from the first end to the second end of the transmission rod, the transmission rod having at least one aperture to allow torque to be coupled to the transmission rod when attaching the first end of the transmission rod to the second end of the mounting device; and an end effector having a first end and a second end, the end effector adapted to receive the ultrasonic vibration from the transmission rod and to transmit the ultrasonic vibration from the first end to the second end of the end effector, the second end of the end effector disposed near an antinode and the first end of the end effector coupled to the second end of the transmission rod.

6. The device of claim 5 further including a coupling member disposed in the at least one aperture of the transmission rod while the transmission rod is vibrating.

7. The device of claim 6 further comprising a compliant member disposed between an outer surface of the coupling member and a wall of the at least one aperture to reduce vibrations from being transmitted to the transmission rod.

8. The device of claim 5 wherein the at least one aperture extends substantially perpendicular to the axis of the transmission rod and extends therethrough.

9. The device of claim 5 further including a wrench having a coupling member, the coupling member configured to be inserted into the at least one aperture of the transmission rod.

10. The device of claim 5 wherein the aperture is disposed near a node.

11. The device of claim 6 wherein the coupling member includes a pin.

12. The device of claim 6 wherein the compliant member substantially surrounds the outer periphery of the coupling member.

13. The device of claim 5 further comprising a non-vibrating member surrounding a portion of the transmission rod, the non-vibrating member including at least one opening coaxially aligned with the at least one aperture of the transmission rod;

a coupling member positionable in the at least one opening of the non-vibrating member and aperture of the transmission rod so that the non-vibration member can rotate the transmission rod.

14. The device of claim 5 further comprising a generator to energize the transducer assembly.

15. The device of claim 5 further comprising a handpiece assembly to carry the transducer assembly.

16. An ultrasonic surgical device comprising:

a transmission component having a first end and a second end, the first transmission component adapted to receive ultrasonic vibration from a transducer assembly and to transmit the ultrasonic vibration from the first end to the second end, the transmission component having an aperture to allow torque to be coupled to the transmission rod.

17. The device of claim 16 further comprising a sheath surrounding, at least partially, and generally radially spaced from the shaft, wherein the sheath includes a pair of flats formed on laterally opposite sides of the hub to form wrench engaging surfaces.

18. The device of claim 17 wherein the wrench flats are fabricated from a plastic material.

19. The device of claim 16 further comprising a coupling member disposed in the aperture of the transmission rod while the transmission rod is vibrating.

20. The device of claim 16 further comprising a sleeve disposed about a wall of the aperture.

21. The device of claim 16 further comprising a pin disposed in the aperture; and a compliant member disposed between an outer surface of the pin and an inner surface of the hole.

22. The device of claim 16 wherein the transmission component has at least two regions of differing cross-sectional dimensions.

23. The device of claim 16 wherein the transmission component is substantially semi-flexible.

24. The device of claim 16 wherein the ultrasonic device includes an endoscopic instrument.

25. The device of claim 16 wherein the ultrasonic device includes an angioplasty catheter assembly.

26. The device of claim 16 wherein the transmission component comprises a wire.

27. An ultrasonic surgical instrument comprising:

a working member having a shaft;

the shaft having a first end and a second end, the shaft adapted to receive ultrasonic vibration and to transmit the ultrasonic vibration from the first end to the second end of the shaft, the shaft having a hole formed therein to allow torque to be applied to the shaft, wherein the shaft being formed without wrench flats.

28. The device of claim 31 further comprising an end effector having a first end and a second end, the end effector adapted to receive the ultrasonic vibration from the shaft and to transmit the ultrasonic vibration from the first end to the second end of the end effector, the first end of the end effector coupled to the second end of the working member.

* * * * *

UNITED STATES PATENT AND TRADEMARK OFFICE
CERTIFICATE OF CORRECTION

PATENT NO. : 5,810,859

DATED : September 22, 1998

INVENTOR(S) : Stephen DiMatteo and Brian Estabrook

It is certified that error appears in the above-identified patent and that said Letters Patent is hereby corrected as shown below:

Claim 16, line 3, delete "first".
Claim 28, line 1, "31" should be --27--.

Signed and Sealed this

Fifteenth Day of June, 1999

Attest:

Q. TODD DICKINSON

Attesting Officer

Acting Commissioner of Patents and Trademarks